United States Patent [19]

Sakurai et al.

[11] 4,211,118
[45] Jul. 8, 1980

[54] ULTRASONIC FAULT DETECTOR

[75] Inventors: Yoshishige Sakurai; Hiroshi Yamada; Kuniharu Uchida, all of Yokohama; Kanekichi Suzuki, Tokyo, all of Japan; Ryoichi Ishii, deceased, late of Yokohama, Japan; by Kyoko Ishii, administrator, Tendo, Japan

[73] Assignee: Tokyo Shibaura Denki Kabushiki Kaisha, Kanagawa, Japan

[21] Appl. No.: 906,699

[22] Filed: May 16, 1978

[30] Foreign Application Priority Data

May 18, 1977 [JP] Japan ................................. 52-56322

[51] Int. Cl.$^2$ .......................................... G01N 29/04
[52] U.S. Cl. ....................................... 73/592; 73/644
[58] Field of Search ................. 73/622, 637, 638, 641, 73/592, 644

[56] References Cited

U.S. PATENT DOCUMENTS

| 3,169,393 | 2/1965 | Stebbins | 73/622 X |
| 4,052,887 | 10/1977 | Sheridan et al. | 73/592 |

*Primary Examiner*—Jerry W. Myracle
*Attorney, Agent, or Firm*—Stevens, Davis, Miller & Mosher

[57] ABSTRACT

An ultrasonic fault detector for inspecting the welds of a welded pipe comprises a casing in which contact medium is contained, an arm movable in the casing, a movable member rotatably secured to the arc, probe heads mounted on the movable member, and a pump for feeding the contact medium to the operating surface of the probe heads. The movable member is constructed to be dividable into two or more parts.

2 Claims, 14 Drawing Figures

ULTRASONIC FAULT DETECTOR

BACKGROUND OF THE INVENTION

This invention relates to an automatic ultrasonic fault detector, particularly useful to detect the faults or defects of welds of a welded pipe.

Nondestructive inspection of the welds of welded pipes has been generally carried out by the use of radioactive rays, ultrasonic wave or electric resistors. However, in a nuclear reactor of a nuclear power plant, when it is required to inspect the welds of the welded pipes, after starting the operation of the reactor, it has been desirable to adopt an ultrasonic fault detecting method because radioactive atmosphere is surrounding the portions to be inspected and the welded pipes are filled with water. Furthermore, the ultrasonic fault detection method is suitable for automatic remote operation for the reason that the detected informations can be remotely indicated.

Generally, in such ultrasonic fault detection methods, it is desired that the ultrasonic fault detector essentially comprises a probe for transmitting and receiving an ultrasonic wave, a probe head for holding the probe, and a contact medium (e.g. water or oil) effectively transmitting the ultrasonic wave to an object to be inspected. In field work, water is usually used only once as the contact medium and discharged at usual inspections, but the water used in a nuclear power plant becomes radioactive and it is expensive to process it to a nonradioactive state. It is therefore desirable to recirculate the radioactive water as the contact medium in the nuclear reactor.

In the prior art, although the ultrasonic fault detection of a large diameter welded pipe was carried out by moving the detector along guide rails, the situation might occur where the load applied on a driving motor will vary thereby periodically varying the gap between the surface of the pipe to be inspected and the probe during the fault detecting operation. Furthermore, ultrasonic fault detection of the welded pipe having a small diameter could not be effectively carried out by the prior art method because the detector is too large for the small pipe, and there has been no efficient ultrasonic fault detector suitable for the reactor container of the nuclear power plant where a number of pipes of small diameters are densely arranged.

SUMMARY OF THE INVENTION

Accordingly, a main object of this invention is to provide an ultrasonic fault detector suitable for remotely inspecting welded portions or the portions near them of the welded pipe of a relatively small diameter.

Another object of this invention is to provide an ultrasonic fault detector in which water serving as the contact medium is recirculated through the detector without discharging it to the outside at every inspection.

A further object of this invention is to provide an ultrasonic fault detector in which several probes having ultrasonic wave emitting angles different from each other can be operated at the same time.

A still further object of this invention is to provide a compact ultrasonic fault detector which is easily detachable from the object to be inspected, exactly detects the position of the fault and precisely discriminates the degree of the fault.

According to this invention, there is provided an ultrasonic fault detector comprising a casing containing contact medium, an arm movable in the casing along the longitudinal axis thereof, a movable member rotatably secured to the arm, a plurality of probe heads mounted on the inside surface of the movable member, and means for feeding the contact medium to the operating surfaces of the probe heads.

BRIEF DESCRIPTION OF THE DRAWINGS

These and the other objects and advantages of this invention will become apparent from the following description made in conjunction with the accompanying drawings, in which.

DESCRIPTION OF THE PREFERRED EMBODIMENT

Figure 1:
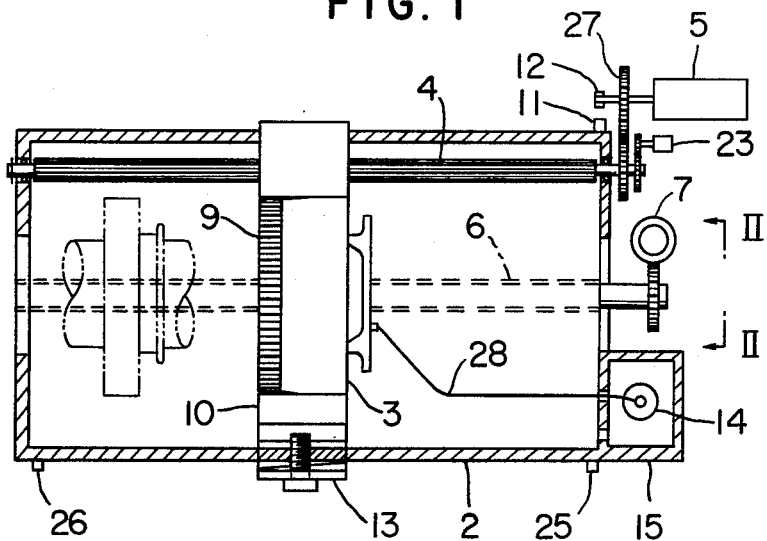
FIG. 1 is a schematic cross-sectional view of one embodiment showing an automatic ultrasonic fault detector according to this invention.
Figure 2:
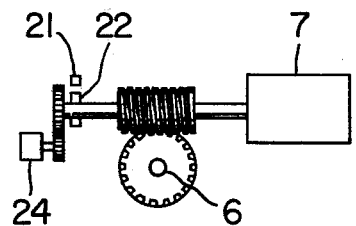
FIG. 2 is a side view of the ultrasonic fault detector as viewed in the direction of an arrow II—II in FIG. 1.

The automatic ultrasonic fault detector according to this invention shown in FIG. 1 comprises an elongated casing 2 containing water, a movable member 3 which is moved longitudinally within the casing while being rotated, a driving motor 5 for rotating the movable member 3 through a driving spline shaft 4, and a slide motor 7 for longitudinally moving the movable member 3 in engagement with a feed screw 6. The movable member 3 is formed as a rotary annular disc and is provided with a ring gear 9 at the outermost periphery of the member, and the ring gear 9 engages the spline shaft 4. The spline shaft 4 is rotatably supported by the casing 2 at its opposite ends and is provided with splines throughout its length, thereby smoothly rotating the movable member 3 even if the member 3 moves to the end of the casing 2. One end of the spline shaft 4 is connected through a gearing 27 with the driving motor 5 which is secured to the casing 2 by a known manner.

The feed screw 6 is rotatably supported in the casing 2 in the longitudinal direction thereof as shown by the dotted lines. This feed screw 6 is driven by the slide motor 7 disposed at one end of the casing 2 and serves to longitudinally move the movable member 3 in engagement therewith. The rotation of the member 3 is detected by a permanent magnet 12 mounted on the rotary shaft of the driving motor 5 and a cooperating reed switch 11 secured to the casing 2, and the axial movement of the member 3 is detected by a permanent magnet 22 mounted on the rotary shaft of the slide motor 7 and a cooperating reed switch 21 secured to the casing 2. Furthermore, the angular position and the axial position of the movable member 3 during the operation are detected by potentiometers 23 and 24. These potentiometers 23 and 24 are of the variable resistor type and accordingly, the angular and the axial positions of the member 3 are detected by the variation of the resistance value.

Figure 3:
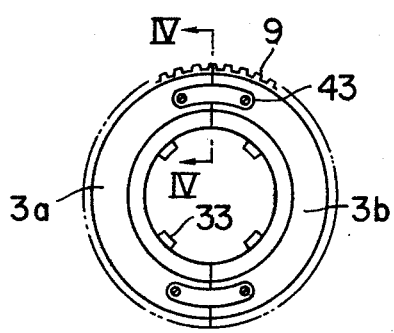
FIG. 3 shows a plan view of a movable member of the ultrasonic fault detector shown in FIG. 1.

Water serving as the contact medium is fed by a pump 14 located in a pump chamber 15 directly connected to and communicating with the casing 2. Limit switches 25 and 26 for limiting the axial displacement of the movable member 3 are attached to the opposite ends of the casing 2, respectively, and serve to stop the operation of the slide motor 7. Referring now to FIG. 3, the annular movable member 3 comprises separable arcuate pieces (3a and 3b) and band pieces 43 which interconnect the arcuate pieces. The ring gear 9 which engages the spline shaft 4 is disposed at the outer periphery of the arcuate pieces, and a plurality of probes 33 for transmitting and receiving ultrasonic waves are mounted on the inside surface of the arcuate pieces.

Figure 4:
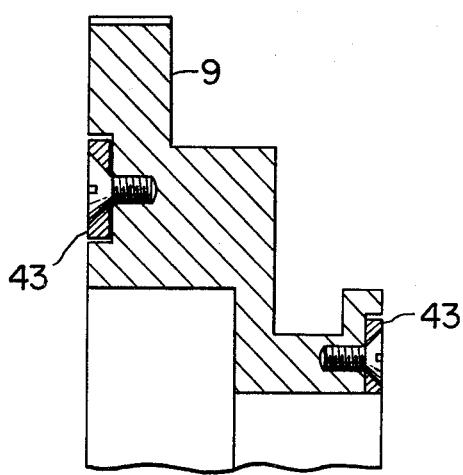
FIG. 4 is a cross-sectional view taken along the line IV—IV in FIG. 1.
Figure 5:
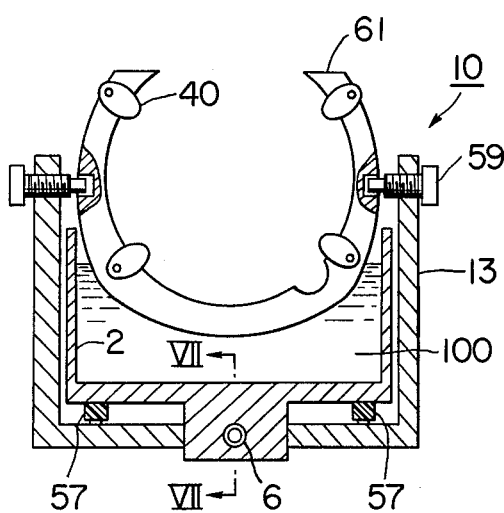
FIG. 5 is a side view showing a movable arm.
Figure 6:
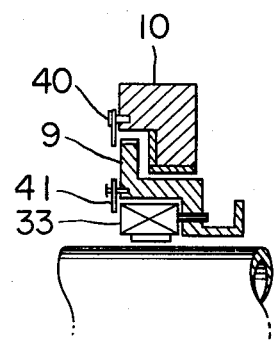
FIG. 6 is a cross-sectional view taken along the line VI—VI shown in FIG. 8.
Figure 7:
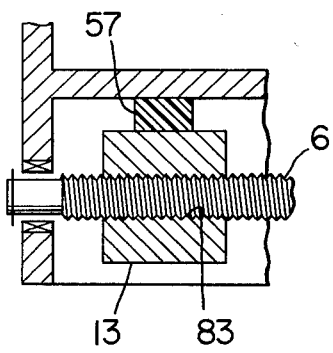
FIG. 7 is a cross-sectional view taken along the line VII—VII shown in FIG. 5.
Figure 12:
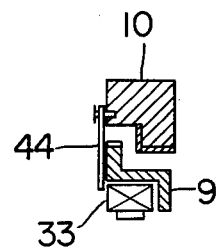
FIG. 12 is a cross-sectional view showing a modification of the mechanism shown in FIG. 6.

The movable member 3 has a multi-step shape in cross section as shown in FIG. 4. FIG. 5 shows that the movable member 3 is rotatably supported by a movable arm 10 which comprises a retaining ring 61, with the upper arcuate portion cut away, and a U-shaped slide arm 13 supporting the retaining ring 61 by pins 59. A plurality of support members 40 are secured to the side surface of the retaining ring 61 with a suitable spacing therebetween as shown in FIGS. 5 and 6. The support members 40 rotatably support the movable member in the retaining ring 61. Support members 61 are adapted to secure the probe heads 33, but larger support members 44 (shown in FIG. 12) may be used for supporting the ring gear 9 and the probe heads 33 instead of the support members 40 and 41.

The U-shaped slide arm 13 is provided with internal threads 83 which are engageble with the external threads of the feed screw 6 and on the upper surface of the slide arm 13 are disposed slide members 57 on which the casing 2 is disposed.

A quantity of water serving as the contact medium 100 is contained in the casing as shown in FIG. 5

Figure 8:
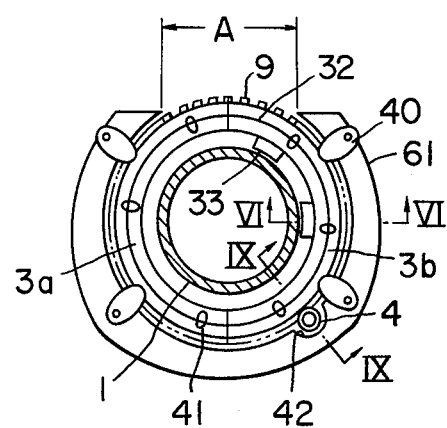
FIG. 8 is a side view showing an assembly of the movable arm and the movable member.
Figure 9:
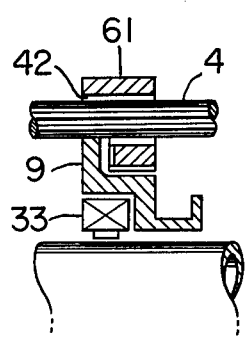
FIG. 9 is a cross-sectional view taken along the line IX—IX shown in FIG. 8.

The movable member 3 is assembled in a manner shown in FIG. 8 in which the retaining ring 61 is proportioned such that the dimension of the opening A of the retaining ring 61 is larger than the outer diameter of the welded pipe to be inspected. The spline shaft 4 to be engaged with the ring gear 9 is received in a groove 42 provided at the lower portion of the retaining ring 61 as shown in FIG. 9.

Figure 13:
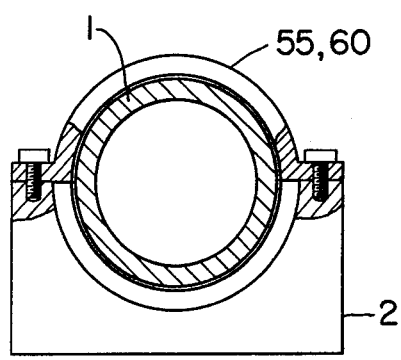
FIG. 13 shows a side view of the detector as viewed from left in FIG. 1.
Figure 14:
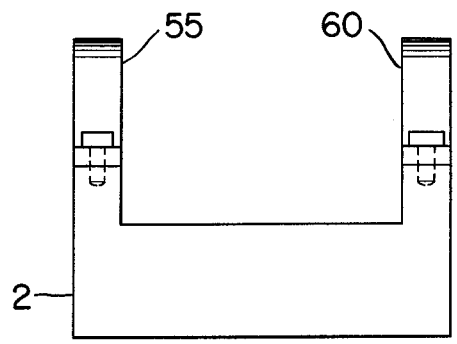
FIG. 14 is a front view of the detector shown in FIG. 13.

FIGS. 13 and 14 show clamping rings 55 and 60 for clamping the pipe 1 for supporting it by the opposite ends of the casing 2. The clamping rings 55 and 60 are semicircular and bolted to the casing. When assembled in this manner, the clamping rings and the casing encircle the pipe being inspected.

Figure 10:
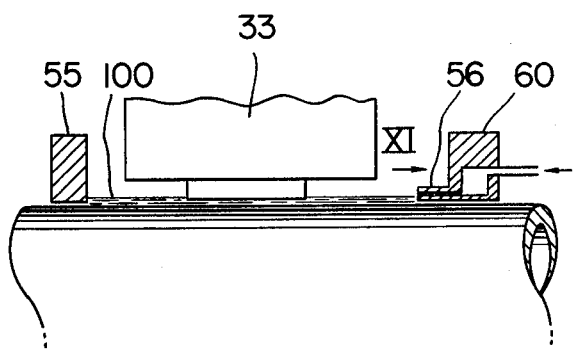
FIG. 10 is a diagrammatic representation of a feeding condition of contact medium.
Figure 11:
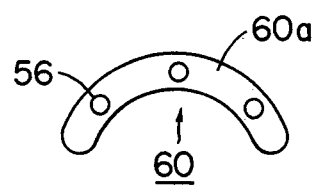
FIG. 11 shows a part of a clamping ring as seen in the direction of an arrow XI in FIG. 10.

A plurality of water supplying nozzles 56 are provided for the clamping ring 60 as shown in FIGS. 10 and 11 and the pump 14 for feeding water is communicated with the nozzles through a pipe 28. The pump 14 is accommodated in the pump chamber 15 located outside of and communicated with the casing 2 so as to make compact the structure of the detector and to make the movable member to move for a maximum extent in the casing 2. The pump chamber 15 can be eliminated if the pump 14 were made to be compact so as not to disturb the movement of the movable member 3. The clamping ring 55 serves also as a water stop member.

The ultrasonic fault detector according to this invention operates as follows.

In case of inspecting the welds of the welded pipe, the movable member 3 is first fit to the pipe 1, this fitting being easily made because the member 3 is constructed to be dividable into two or more parts. The casing 2 is then secured to the pipe 1 by the clamping rings 55 and 60. The retaining ring 61 is applied to the member 3 and fixed thereto by the support members 40. Thus, the attachment of the detector to the pipe 1 is completed. Then the driving motor 5 and the slide motor 7 are operated to move and rotate the movable member 3 in the casing 2 so as to start the ultrasonic fault detection. During the fault detection operation, water is supplied to the operating surfaces of the probe heads 33 by means of the pump 14, and the axial movement of the movable member 3 is limited by the reed switches 25 and 26. The water fed from the pump 14 is circulated through the pipe 28, the nozzles 56, the casing 2 and the pump chamber 15.

As described hereinabove, since the ultrasonic fault detector according to this invention can easily be fit to the pipe to be inspected, the fault detection of a considerably long pipe can easily be carried out and the fault detection of the pipes of different diameters can also be carried out by using movable members of different diameters. The movable member can be moved axially and rotated, independently, so that the position of the fault of the weld of the pipe can be exactly inspected and detected. Furthermore, since the contact medium, water, is used cyclically, it is not necessary to supplement any fresh water, thereby preventing the contamination of the external environment where pipes of a nuclear reactor are inspected.

What is claimed is

1. An ultrasonic fault detector comprising a casing containing contact medium, an arm movable in said casing along the longitudinal axis thereof, a movable member rotatably secured to said arm, said movable member being divided into two or more parts, a plurality of probe heads mounted on the inside surface of said movable member, and means for feeding the contact medium to the operating surfaces of said probe heads.

2. An ultrasonic fault detector comprising a casing containing contact medium, said casing having an open top, an arm movable in said casing along the longitudinal axis thereof, a movable member rotatably secured to said arm, a plurality of probe heads mounted on the inside surface of said movable member, means for feeding the contact medium to the operating surfaces of said probe heads, and a removable clamping member, said clamping member being secured to said casing whereby said casing and clamping member encircle an object to be inspected.

* * * * *